(12) United States Patent
Ghisalberti

(10) Patent No.: US 6,953,583 B1
(45) Date of Patent: Oct. 11, 2005

(54) USE OF CONJUGATED LINOLEIC ACID (CLA) FOR THE TOPICAL TREATMENT OF CELLULITE

(75) Inventor: Carlo Ghisalberti, São Paulo (BR)

(73) Assignee: Pentapharm AG, (CH)

( * ) Notice: Subject to any disclaimer, the term of this patent is extended or adjusted under 35 U.S.C. 154(b) by 0 days.

(21) Appl. No.: 10/088,004

(22) PCT Filed: Sep. 8, 2000

(86) PCT No.: PCT/IB00/01280

§ 371 (c)(1),
(2), (4) Date: Jun. 5, 2002

(87) PCT Pub. No.: WO01/17498

PCT Pub. Date: Mar. 15, 2001

(30) Foreign Application Priority Data

Sep. 9, 1999 (IT) .............................. MI99A1894

(51) Int. Cl.[7] .............................. A61K 6/00; A61K 7/00
(52) U.S. Cl. ...................... 424/401; 424/646; 514/263; 514/264; 514/558; 514/860
(58) Field of Search .......................... 424/400, 401, 424/646; 514/263, 264, 558, 860

(56) References Cited

U.S. PATENT DOCUMENTS

| | | | |
|---|---|---|---|
| 4,393,043 A * | 7/1983 | Koulbanis et al. | 424/59 |
| 5,208,356 A * | 5/1993 | Pariza et al. | 554/79 |
| 5,667,793 A * | 9/1997 | Cho et al. | 424/401 |
| 6,019,990 A * | 2/2000 | Remmereit | 424/401 |
| 6,136,985 A * | 10/2000 | Millis | 549/23 |
| 6,444,234 B1 * | 9/2002 | Kirby et al. | 424/725 |
| 2001/0041708 A1 * | 11/2001 | Halvorsen et al. | 514/264 |

FOREIGN PATENT DOCUMENTS

| | | |
|---|---|---|
| EP | 1 010 424 | 6/2000 |
| WO | WO 90/12563 A1 * | 11/1990 |
| WO | WO 98/17269 | 4/1998 |
| WO | WO 99/12538 | 3/1999 |
| WO | WO 99/26588 A2 * | 6/1999 |
| WO | WO 99/32105 | 7/1999 |
| WO | WO 00/01351 | 1/2000 |
| WO | WO 00/12080 A1 * | 3/2000 |
| WO | WO 00/37040 | 6/2000 |

OTHER PUBLICATIONS

Brodie et al. Conjugated linoleic acid inhibits differentiation of pre- and post- confluent 3T3-L1 preadipocytes but inhibits cell proliferation only in preconfluent cells. J Nutr. Mar. 1999;129(3):602-6.

Rosenbaum et al. An exploratory investigation of the morphology and biochemistry of cellulite. Plast Reconstr Surg. Jun. 1998;101(7):1934-9.

Merlen et al. Cellulitis, a conjunctive microvascular disease. Phlebologie. Jul.-Sep. 1979;32(3):279-82. French.

Smith, W.P. Cellulite Treatments: Snake oils or skin science. Cosmetics & Toiletries, 1995, 110: 61-70.

* cited by examiner

*Primary Examiner*—Gary Kunz
*Assistant Examiner*—Marina Lamm
(74) *Attorney, Agent, or Firm*—Fish & Richardson P.C.

(57) ABSTRACT

The present invention relates to the use of conjugated linoleic acid (CLA) for the topical treatment of fatty deposits and cellulite and to new topical compositions and to cosmetic and dermatological topical compositions for the treatment of fatty deposits and cellulite comprising CLA as well as kits comprising CLA for said treatment.

8 Claims, No Drawings

USE OF CONJUGATED LINOLEIC ACID (CLA) FOR THE TOPICAL TREATMENT OF CELLULITE

FIELD OF THE INVENTION

The present invention relates to the use of conjugated linoleic acid (CLA) for the topical treatment of fatty deposits and cellulite and to new topical compositions.

More particularly, the invention relates to cosmetic and dermatological topical compositions for the cosmetic treatment of fatty deposits and cellulite comprising CLA as well as kits comprising CLA for said treatment.

BACKGROUND OF THE INVENTION

Conjugated linoleic acid (CLA) is a mixture of positional and configurational isomers of octadecadienoic acid, which are naturally occurring substances found in milk and diary products as well as in meats of ruminants.

The term CLA includes the family of positional and configurational isomers of C18:2 fatty acid, more precisely the cis and trans form of 9,11-10,12- and 11,13-octadecadienoic acids.

Many studies reported that synthetic CLA is an effective agent in inhibiting mammary, colon, forestomach, and skin carcinogenesis in experimental models, due to its modulation of lymphocyte and macrophage activities. Recent clinical and in vivo data disclosed novel biological effects of CLA, e.g. the anti-atherogenic and anti-hyperinsulinemic activities.

After having attracted the attention of the international scientific community for its therapeutic properties above, CLA is gaining further consumer acceptance as nutritional supplement as it has been shown that a CLA-enriched diet produces a significant improvement in overall health conditions.

CLA is also known as a slimming agent, whose oral consumption produces a marked decrease of body fat with increase in the lean body mass. The effects of CLA on body fat/lean ratio seem to be due to inhibition of both proliferation and differentiation of preadipocytes, as observed by Brodie A. E. et al. in J. Nutr. 129:602–6 (1999).

The use of CLA in topical composition and cosmetic method for treating skin conditions selected from the group consisting of wrinkling, sagging, photodamaged skin, sensitive skin, dry skin, flaky skin, red skin, irritated skin, itchy skin and age spots, is disclosed in WO0037040.

Topical compositions of zinc salts of CLA for the treatment of skin disorders, such as eczema, psoriasis and dermatitis and so on WO98/17269 discloses. However, the use of zinc salts of CLA is limited to pharmaceutical and dermatological purposes only. Moreover, the poor solubility of the zinc salts of CLA, either in lipophilic and hydrophilic media, significantly decreases the bioavailability of the active ingredient in said topical treatment.

DETAILED DESCRIPTION OF THE INVENTION

It is appreciated that in the present specification the term CLA is intended to include either CLA in the form of free fatty acid or its derivatives, such as its phospholipid, its mono-, di- and tri-glycerides, ethers, esters or salts thereof. All derivatives must be physiologically acceptable, i.e. non-toxic derivatives of CLA. Preferred salts of CLA include the metallic soaps of CLA with alkaline and/or earth-alkaline ions, such as sodium, potassium, or magnesium ions, and the nitrogen-containing salts, such as ammonia, mono- di- or tri-ethanolamine.

We have first envisaged the possibility to use CLA in the treatment of cellulite, the skin dimpling of the thighs and buttocks caused by dermohypodermosis and oedemato-sclerous panniculopathy, in which the fibroblastic reaction predominates over capillaro-veinular changes.

As observed by Rosenbaum M; Prieto V; Hellmer J; Boschmann M; Krueger J; Leibel R L; Ship A G (Plast Reconstr Surg, 101 (7):1934–9 1998), in vitro pathologic examination of wedge biopsies and in vivo sonographic examination of the thigh both showed a diffuse pattern of extrusion of underlying adipose tissue into the reticular dermis.

Adipocytes of exaggerated size interpenetrate into micronodules and later into macronodules marked off by more or less structured conjunctive fibrilla, as quoted by Merlen J F; Curri S B; Sarteel A M (Phlebologie, 32(3): 279–82, 1979).

Due the uncertainty of cellulite aetiology, said unaesthetic condition has been so far treated with a variety of active ingredients, each acting by different mechanisms.

We have now found out that the topical administration of CLA accelerates and provokes the reduction of fatty deposits.

We have consequently found out that CLA is effective in the topical treatment of the impaired aesthetic conditions caused by subcutaneous fat deposition, particularly on pannicular adiposis, said topical treatment leading to a significant improvement of the cellulite conditions.

Therefore, one of the objects of the present invention is the use of CLA for the topical treatment and/or prevention of fatty deposits and cellulite.

CLA is particularly suitable for the topical anticellulite treatment; it is a natural product which showed no observed adverse effects or toxicity in humans after topical treatment. After several applications on people of both sexes having derma either in normal or in pathological status, e.g. erythema and itching derma, no phenomena showing intolerance to the product occurred.

The physical and chemical properties of CLA are particularly appropriate for a topical skin treatment, as it displays good lipid solubility and is easily absorbed onto the horny layer.

According to another of its aspects, the present invention concerns a cosmetic and dermatological topical composition, useful for treating and/or preventing cellulite and fatty deposits.

According to a further aspect, the invention concerns a method for the treatment of cellulite which comprises topically administering to a subject an effective amount of CLA, either alone or in the form of a topical composition.

In order to exploit the cosmetic treatment of the invention CLA is preferably administered in the form of a topical composition, said composition having a content of CLA of from 0.5 to 70% by weight, preferably from 1 to 30% by weight, more preferably from 2 to 5% by weight, optionally in admixture with suitable customary auxiliary agents.

In a preferred embodiment of the present invention, CLA is combined with one or more well-known anti-cellulite agent.

Particularly preferred common common anti-cellulite agents are substances showing beta-stimulation (adrenergic beta-agonists) to further enhance lipolysis into the dermal adipocytes. Examples of such substances are xanthines such as caffeine, theophylline, theobromine and aminophylline, which are characterized by a high skin availability and an high efficacy. Xanthines are preferably employed in an proportion of at least 0.05%, generally in an proportion of from 0.05% to 20%, preferably from 0.10% to 10%, optimally from 0.5% to 3.0% by weight of the composition in order to maximize efficacy at optimum cost.

Other preferred common anti-cellulite agents are substances acting as collagen synthesis stimulators, such as ascorbates and triterpenoids of *Centella asiatica*, e.g. asiatic acid, madecassic acid, asiaticoside, madecaside, inositol phosphate, and phytic acid.

Other preferred common anti-cellulite agent are substances which improve the poor vascularity condition associated to the cellulitic areas by a vasokinetic activity, such as minoxidil, nicotinates, escin, ivy, and methyl salicylate.

Other preferred common anti-cellulite agent are natural substance exerting adenylate cyclase agonist and/or anti-phosphodiesterase activities, which accelerate the reduction of fatty deposits located in the cellulite affected area. The former group may include extracts from *Ipomea* spp., from *Salvia* spp. and from *Rosmarinus officinalis*, the latter group the yohimbine-type alkaloids and those plant extracts (e.g. ginkgo biloba) which contain dimeric flanones such as amentoflavone, bilobetine, sciadopitisine, ginkgonetine, or extracts from some Malvaceae (e.g. *Malva, Althea, Hibiscus, Hoheria, Sidalcea, Abutilon* and *Gossypium*).

For the treatment of cellulite and fatty deposits, topical CLA may also be used in combination with vanadium compounds.

Vanadium compounds are known to act as insulin-mimetic substances, thus as being capable to enhance glycolisis and metabolic turn-over in cells, including adipocytes.

Therefore, according to a particular embodiment, the present invention relates to a cosmetic composition comprising CLA and at least a vanadium compound.

Vanadium (IV) or (V) compounds are suitably present at concentration in the range of $10^{-10}$ to $10^{-3}$ moles/kg, preferably $10^{-7}$ to $10^{-5}$ moles/kg in the cosmetic compositions of the present invention.

Illustrative examples of suitable vanadium (V) compounds useful in the practice of the present invention include sodium metavanadate ($NaVO_3$), orthovanadate ($Na_3VO_4$) and pyrovanadate ($Na_4V_2O_7$), corresponding salts with potassium ($KVO_4$), ammonium ($NH_4VO_3$), calcium ($Ca_3(VO_4)_2$), iron ($Fe(VO_3)_3$), and corresponding salts of vanadates with magnesium, zinc, aluminum, and the like; the vanadium (V) oxides such as the pentoxide ($V_2O_5$), oxytrichloride ($VOCl_3$), oxytribromide ($VOBr_3$) and the like, as well as polymers such as a dimer ($H_2V_2O_7$), a trimer ($V_3O_9$), a decamer ($HV_{10}O_{28}$), and the like.

Illustrative examples of suitable vanadium (IV) compounds useful in the practice of the present invention include vanadyl sulfate ($VOSO_4$), and corresponding compounds with acetate, etc; vanadium (IV) oxyhalides such as the oxychloride ($VOCl_2$), oxydibromide ($VOBr_2$), and oxydifluoride ($VOF_2$): vanadium (IV) halides such as the tetrachloride ($VCl_4$), tetrabromide ($VBr_4$) and tetrafluoride ($VF_4$) and the like; vanadium dioxide ($VO_2$) and vanadium tetraoxide ($V_2O_4$).

Furthermore, the vanadium (IV) or (V) compounds may be present in form of chelates, clathrates or other complexes, including those with amino acids, proteins, peptidic growth factors, nucleic acids, phosphates, phospholipids, fatty acids, prostaglandins, AHAs, retinoids, tris-edatate, glycols, catechols, glutathione, and the like.

The vanadium (IV) or (V) compounds may also be present as salts of organic acids and vanadium contained in tunicates (sea squirts), some mushroom species and plants, and other organic sources. Specific examples of vanadium organometallic compounds include vanadyl salts of organic acids such as: vanadyl linoleate, oleate, palmitate, phenolate, resinate and stearate.

All the compositions according to the invention may also comprise any cosmetically acceptable ingredients. The expression "cosmetically acceptable ingredients" designate in the present specification products which are suitable for their use in cosmetic treatments, for example those included in the INCI list drawn by the European Cosmetic Toiletry and Perfumery Association (COLIPA) and issued in 96/335/EC "Annex to Commission Decision of 8 May 1996".

A variety of active ingredients may further be added to the compositions according to the present invention. Although not limited to this category, general examples include anti-inflammatory agents and skin whitening agents, antioxidants and anti-wrinkling agents.

Suitable anti-inflammatory compounds include, but are not limited to, rosmarinic acid, glycyrrizinate derivatives, alpha bisabolol, azulene and derivatives thereof, asiaticoside, sericoside, ruscogenin, escin, escolin, quercetin, rutin, betulinic acid and derivatives thereof, catechin and derivatives thereof.

Suitable skin whitening compounds include, but are not limited to, ferulic acid, hydroquinone, arbutine, and kojic acid.

Suitable antioxidants and anti-wrinkling compounds include, but are not limited to, retinol and derivatives, tocopherol and derivatives, salicylates and their derivatives.

Another important agent which can be added in the cosmetic composition according to the invention is an alpha-hydroxy acid. Preferred alpha-hydroxy acids are monocarboxylic acids, improving skin penetration and efficacy of CLA and further common anticellulite agents, such as lactic acid, glycolic acid, mandelic acid and mixtures thereof. Preferably, the proportion of the alpha-hydroxy acid component in the cosmetic composition of the invention is from 1.5% to 15%, more preferably from 3.0% to 12.0% by weight of the composition.

Another important optional ingredient is chosen among essential fatty acids (EFAs), exerting an important role in skin defence against oxidative stress, by entering in the lipid biosynthesis of epidermis and providing lipids for the barrier formation of the epidermis. Preferred essential fatty acids are selected from the group consisting of linoleic acid, gamma-linolenic acid, homo-gamma-linolenic acid, columbinic acid, eicosa-(n-6,9,13)-trienoic acid, arachidonic acid, gamma-linolenic acid, timnodonic acid, hexaenoic acid and mixtures thereof.

The cosmetic compositions of the invention can further comprise substances acting as dilutant, dispersant or carrier for CLA which are added to the compositions according to well known techniques in any suitable proportion well known to the skilled in the art, for example ranging from about 30% to about 99.9%, preferably from about 50 to 99.5% by weight of the total composition.

An oil or oily material may be present with water together with an emulsifier (alias "surfactant") to provide either w/o or o/w emulsions, largely depending on the average hydrophilic-lipophilic balance (HLB) of the emulsifier. Surfactants can be incorporated in any suitable proportion well known to the skilled in the art, for example from about 0.5% to about 30%, preferably from about 1% to about 15% by weight.

Cationic, nonionic, anionic, or amphoteric surfactants, and combinations thereof may also be employed. Nonionic surfactants may include alkoxylated compounds based upon fatty alcohols, fatty acids and sorbitan, copolymers of polyoxypropylene-polyoxyethylene, and alkyl polyglycosides. Anionic-type surfactants may include fatty acid soaps, sodium lauryl sulphate, sodium lauryl ether sulphate, alkyl benzene sulphonate, mono and/or dialkyl phosphates and the like. Amphoteric surfactants include dialkylamine oxides, various types of betaines and natural phospholipids.

In a water-based cosmetic composition, a thickener agent may also be present in any suitable proportion well known to the skilled in the art, for example from 0.1 to 10% by weight, preferably from about 0.5% to 5% by weight. Exemplary thickener agent are cross-linked polyacrylate materials (Carbopol®), and gums such as xanthan, carrageenan, gelatin, karaya, pectin and locust beans gum. Said water-based cosmetic composition can be protected with preservatives against the growth of microorganisms. Suitable preservatives include alkyl esters of p-hydroxybenzoic acid, hydantoin derivatives, propionate salts, methyl paraben, propyl paraben, imidazolidinyl urea, sodium dehydroxyacetate benzyl alcohol, and a variety of quaternary ammonium compounds. Preservatives are added any suitable proportion well known to the skilled in the art, for example in proportion ranging from about 0.2% to 1% by weight.

In a fluid non-aqueous cosmetic composition, silicone polymers may also be present, in any suitable proportion well known to the skilled in the art, for example in amounts of ranging from 5 to 95% by weight.

Further ingredients that may be included in the cosmetic composition of the present invention are emollients. Under certain circumstances emollients may have dual functionality, acting both as carrier, to facilitate the dispersion of the CLA as active ingredient and skin softners. Emollients may be incorporated in the cosmetic composition of the invention in any suitable proportion well known to the skilled in the art, for example ranging from about 0.5% to about 50%. Suitable emollients may be classified under such general chemical categories as esters, fatty acids and alcohols, polyols and hydrocarbons. Appropriate fatty di-esters include dibutyl adipate, diethyl sebacate, diisopropyl dimerate, propylene glycol myristyl ether acetate, diisopropyl adipate, and dioctyl succinate. Appropriate branched chain fatty esters include 2-ethyl-hexyl myristate, isopropyl stearate and isostearyl palmitate. Appropriate tribasic acid esters include triisopropyl trilinoleate, trilauryl citrate, tributirrine, and saturated or unsaturated vegetable oils. Appropriate straight chain fatty esters include lauryl palmitate, myristyl lactate, oleyl eurcate, stearyl oleate coco-caprylate/caprate, and cetyl octanoate. Appropriate fatty alcohols and acids are $C_{10}$–$C_{20}$ compounds such as cetyl, myristyl, palmitic and stearyl alcohols and acids. Appropriate polyols are linear and branched chain alkyl polyhydroxyl compounds, such as propylene and butylene glycol, sorbitol glycerin, as well as polymeric polyols such as polypropylene glycol and polyethylene glycol. Appropriate hydrocarbons are linear $C_{12}$–$C_{30}$ hydrocarbon chains such as mineral oil, petroleum jelly, squalene and isoparaffins.

Sunscreens may also be incorporated in the cosmetic composition of the invention. Illustrative compounds are the derivatives of PABA, cinnamate and benzophenone such as octyl methoxy-cinnamate, 2-hydroxy-4-methoxy-benzophenone. The proportion of sunscreens employed depends upon the degree of protection desired from the UV radiation.

Other minor components may also be added to the cosmetic composition of the invention, including colouring agents, opacifiers and perfumes each being optionally present in appropriate proportions for example from 0.001% up to 20% by weight of the composition.

The topical skin treatment composition of the invention can be formulated as a lotion, a fluid cream, a cream or a gel. The composition can be packaged in a suitable container according to its viscosity and to the intended use by the user. For example, a lotion or fluid cream can be packaged in a bottle, in a roll-ball applicator, in a capsule, in a propellant-driven aerosol device or a container fitted with a pump suitable for finger operation. When the composition is a cream, it can simply be stored in a non-deformable bottle or in a squeeze container, such as a tube or a lidded jar.

According to another of its aspects the present invention relates to a kit for the topical administration of CLA.

Said kit comprises (a) unit dosage form compositions comprising CLA, optionally in admixture with suitable customary excipients and antioxidants, preferably in the form of an oily liquid and (b) unit dosage form comprising at least one hydrophilic anticellulite agent, optionally in admixture with suitable customary excipients and alpha-hydroxy acid, in aqueous or hydroalcoholic solution.

The kit packaging box further comprises an leaflet giving the instruction to apply first the aqueous solution (b) for the effective absorption of the hydrophilic ingredients, and secondly to apply the oily liquid (a).

One of the advantages of the kit is that the penetration of hydrophilic anticellulite agents is made easier in absence of the oily phase, which is subsequently applied to the skin.

The following examples show in detail how the present invention can be practiced but should not be intended as limiting it.

PREPARATIVE EXAMPLE 1

Synthesis of CLA by Alcaline Isomerization of Grape Seed Oil in Glycerol (The following synthesis makes the object of a co-pending application).

1 kg glycerol, 235 g potassium hydroxide (KOH) and 1000 g of grape seed oil were added into a 4-neck round bottom flask (5000 ml) equipped with a mechanical stirrer, a thermometer, a reflux condenser, and a nitrogen inlet, the nitrogen being introduced in first run through two oxygen traps.

Nitrogen was bubbled into the reaction mixture for 20 min and the temperature was then raised to 90–100° C., and kept under mechanical stirring for about 20 minutes to convert the trigliceride in the corresponding potassium salts. The double phase system disappears to form a glyceric soap suspension, then heated at 230° C. under inert atmosphere and stirred for 4 hours.

The reaction mixture was cooled to about 100° C., and the stirring stopped as the reaction mixture tend to reach very high viscosity during cooling. 2 l of water was then slowly added, and the mixture kept at 95° C. for 2 hour. This operation becomes necessary because of the neglegible presence of water and high content of glycerol causing fatty acids to be present as mono- and diglyceride from 5% to 10% by weight of the total lipid content. As partial glyceride esters tend to form W/O emulsion, the water addition and re-heating provides full saponification of the residual esterified fatty acid.

The mixture was transferred into a becker, then cooled to room temperature and 50% w/v sulfuric acid was added to the mixture which was stirred for 1 hour until the pH stabilized at about 3.

The acidulated oil phase formed a lower hydroglyceric layer and an upper fatty acid oil layer containing CLA, which was separated by decantating. Noteworthy, in industrial operation the separation could be carried out by centrifugation.

The CLA was washed with water and finally it was made anhydrous with sodium sulphate and filtered, then it is stored in a dark bottle at 4° C. until time of use. Total yield about 770 g af an amber oil, whose GC-analysis is shown in Table 1.

TABLE 1

| Fatty Acid | Grape Seed (Starting material) | CLA from Grape Seed (Final Product) |
|---|---|---|
| C14:0 | 0.11 | 0.13 |
| C16:0 | 6.53 | 6.56 |
| C18:0 | 3.02 | 3.23 |
| C20:0 | 0.19 | 0.20 |
| total saturated | 9.85 | 10.12 |
| C16:1 | 0.42 | 0.48 |
| C18:1 | 16.42 | 17.15 |
| C18:1(t) | 0.08 | 0.23 |
| C20:1 | 0.59 | 0.60 |
| total monounsaturated | 17.51 | 18.46 |
| C18:2 | 72.11 | 1.76 |
| C18:2-conjugated (CLA) | 0.21 | 69.48 |
| C18:3 | 0.31 | 0.18 |
| C20:3 | 0.01 | 0.00 |
| total polyunsaturated | 72.64 | 71.42 |

The composition of CLA appears to be a complex mixture, i.e. 9c, 11t- and 8c, 10t-octadecadienoic acids at 30.90%, 11c, 13t-10t, 12c-octadecadienoic acids at 32.05%, 11t, 13c-8c, 10c-9c, 11c-octadecadienoic acid at 1.55%, 10c, 12c-11c, 13c-11t, 13t, 9t, 11t-10t, 12t-8t,10t-octadecadienoic acids making the remaining part.

COMPARATIVE EXAMPLE 1 AND APPLICATIVE EXAMPLES 1,2

Body Creams

Three different O/W emulsions were prepared under stirring by turbomixing the oily phase and the water phase, each separatedly preheated at 75° C.; the compositions are shown herewithafter:

| Ingredient | Emulsion of Comparative Example 1 | Emulsion of Applicative Example 1 | Emulsion of Applicative Example 2 |
|---|---|---|---|
| Oily phase | | | |
| CLA from the Preparative Example 1 | — | 2.7 g | 2.7 g |
| soybean fatty acids | 2.7 g | — | — |
| poliglyceryl-2-sesquistearate | 1.0 g | 1.0 g | 1.0 g |
| bees wax | 0.3 g | 0.3 g | 0.3 g |
| magnesium stearate | 0.5 g | 0.5 g | 0.5 g |
| aluminum stearate | 0.5 g | 0.5 g | 0.5 g |
| hydrogenated castor oil 7-PEO | 2.0 g | 2.0 g | 2.0 g |
| liquid paraffine | 10.0 g | 10.0 g | 10.0 g |

-continued

| Ingredient | Emulsion of Comparative Example 1 | Emulsion of Applicative Example 1 | Emulsion of Applicative Example 2 |
|---|---|---|---|
| methyl p-hydroxybenzoate | 0.1 g | 0.1 g | 0.1 g |
| 18-beta-glycirretic acid | 1.0 g | 1.0 g | 1.0 g |
| alpha-tocopheryl acetate | 0.5 g | 0.5 g | 0.5 g |
| BHT | 0.3 g | 0.3 g | 0.3 g |
| Aqueous phase | | | |
| glycolic acid | 3.0 g | 3.0 g | 3.0 g |
| matè extract (caffeine 7%) | — | — | 2.0 g |
| decaffeinated mate extract | 2.0 g | 2.0 g | — |
| ascobic acid (vitamin C) | 0.01 g | 0.01 g | 0.01 g |
| deionized water q.b. | to 100 g | to 100 g | to 100 g |

As it can be noted, the topical formulations contain no CLA, CLA alone, and CLA with caffeine, respectively.

APPLICATIVE EXAMPLE 3

Clinical Trial of Anticellulite Activity by Topical Application of CLA and CLA with a Xantine 9 female subjects were selected based on their cellulite intensity in the thigh area having a bi-lateral symmetry. Subjects with grades 1 and 2 cellulite were chosen, as a 5-point grading scale was used to rate the cellulite severity of each subject. The scale ranged from 0 to 4, being 0=No cellulite; 1=Small bumps or depressions; 2=Striations and bumps; 3= Pronounced lumpiness of the skin and striations; 4=All of the above plus hard sub-surface nodules.

The subjects were divided in 3 groups of 3 individuals each, and instructed to apply in the right thigh the compositions of Comparative Example 3, the one of Applicative Example 4, and the one of Applicative Example 5, respectively.

The subject were taught to carried out the application two times a day, at morning and at night, during 2 months. Afterwards the cellulite condition were evaluated according Smith W P (Cosmetics & Toiletries, 61–70, June 1995), by comparison of the right thigh versus left thigh. Results are illustrated in Table 2.

TABLE 2

Change of the cellulite condition after 2 month application

| Condition | Cream of Comparative Example 3 | Cream of Applicative Example 4 | Cream of Applicative Example 5 |
|---|---|---|---|
| Thigh diameter | −1% | −5% | −8% |
| Fatty layer thickness | −3% | −18% | −24% |
| Subjective improvement | +10% | +33% | +50% |
| Clinical grading | +2% | +30% | +30% |
| Skin firmness | +5% | +10% | +15% |
| Irritation reactions | 2 | 0 | 3 |
| Skin hydration | +25% | +13% | +24% |
| Surface smoothness | +14% | +21% | +37% |

The results above show that the composition containing CLA effectively ameliorate the cellulite condition, with a further improvement by the combination with caffeine.

APPLICATIVE EXAMPLE 4

Kit for the Cellulite Treatment

An oily mixture (a) and a hydroalcoholic solution (b) were separately prepared by blending the following ingredients:

| CLA from the Preparative | |
|---|---|
| a) Ingredient of the oily mix | |
| Example 1 | 1.50 g |
| soya sterols | 0.25 g |
| butylene glycol | 1.50 g |
| vitamin E acetate | 0.20 g |
| vitamin A palmitate | 0.20 g |
| alpha bisabolol | 0.10 g |
| asiaticoside | 0.15 g |
| ethyl alcohol 94° | 5.00 g |
| almond oil | q.b. to 20.00 ml |
| a) Ingredient of the aqueous mix | |
| tributyl citrate | 0.15 g |
| caffeine | 0.15 g |
| ginkgo biloba extract | 0.50 g |
| green tea extract | 0.10 g |
| theophylline | 0.20 g |
| glycolic acid | 3.00 g |
| escin | 0.05 g |
| 18-beta-glycirretic acid | 0.03 g |
| disodium EDTA | 0.02 g |
| ethyl alcohol 94° | 2.00 g |
| demineralized water | q.b. to 20 ml(*) |

(*)Due to the low pH value, preservatives are not needed.

The two compositions were separately bottled in 25 ml jars and combined in the same kit package, along with the instruction to firstly apply (b) and, after 10 minutes to apply (a).

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A method of treating fatty deposits and cellulite of a person, comprising:
    determining the presence of dimpled skin of the person; and
    contacting the skin with a composition comprising:
        from 2 to 70 weight percent of at least one of:
            (a) at least one conjugated linoleic acid as a free acid or a combination of conjugated linoleic acids, each of the conjugated linoleic acids of the combination being a free acid, (b) at least one salt of at least one conjugated linoleic acid, the salt comprising at least one an alkaline metal, an alkaline earth, ammonia, monoethanolamine, diethanolamine, and triethanloamine, and (c) a combination of (a) and (b).

2. The method of claim 1, wherein the composition comprises a member selected from the group consisting of cis and trans isomers of 9,11; 10,12; and 11,13 octadecadienoic acid, and phospholipid, mono, di and tri glycerides, ethers, esters, and salts thereof.

3. The method of claim 1, wherein the composition is at least one of a cream, a gel, a lotion, an oil, and a spray.

4. The method of claim 1, wherein the composition comprises anti cellulite agents.

5. The method of claim 4, wherein the anti cellulite agent is a xanthine.

6. The method of claim 4, wherein the anti cellulite agent is selected from the group consisting of caffeine, theophilline, theobromine, aminophylline and a combination thereof.

7. The method of claim 1, wherein the composition further comprises a vanadium compound.

8. The method of claim 1, wherein the step of determining the presence of at least one of fatty deposits and cellulite comprises visually determining the presence of dimpled skin.

* * * * *